United States Patent
Esch

(10) Patent No.: US 10,927,335 B2
(45) Date of Patent: Feb. 23, 2021

(54) MICROFLUIDIC BODY-ON-A-CHIP DEVICE AND METHODS OF USE THEREOF

(71) Applicant: CORNELL UNIVERSITY, Ithaca, NY (US)

(72) Inventor: Mandy Brigitte Esch, Syracuse, NY (US)

(73) Assignee: Cornell University, Ithaca, NY (US)

( * ) Notice: Subject to any disclaimer, the term of this patent is extended or adjusted under 35 U.S.C. 154(b) by 2 days.

(21) Appl. No.: 15/765,073

(22) PCT Filed: Oct. 3, 2016

(86) PCT No.: PCT/US2016/055185
§ 371 (c)(1),
(2) Date: Mar. 30, 2018

(87) PCT Pub. No.: WO2017/059436
PCT Pub. Date: Apr. 6, 2017

(65) Prior Publication Data
US 2018/0273888 A1    Sep. 27, 2018

Related U.S. Application Data

(60) Provisional application No. 62/235,782, filed on Oct. 1, 2015.

(51) Int. Cl.
*C12M 3/06*    (2006.01)
*C12M 1/00*    (2006.01)
(Continued)

(52) U.S. Cl.
CPC ............ *C12M 23/16* (2013.01); *C12M 21/08* (2013.01); *C12M 29/00* (2013.01); *G01N 33/5082* (2013.01)

(58) Field of Classification Search
CPC ...... C12M 23/16; C12M 29/00; C12M 21/08; G01N 33/5082
See application file for complete search history.

(56) References Cited

U.S. PATENT DOCUMENTS 4,963,490 A    10/1990 Churchhouse et al.
6,196,805 B1    3/2001 Reilley
(Continued)

OTHER PUBLICATIONS

International Preliminary Report on Patentability corresponding to PCT/US2016/055185, dated Apr. 12, 2018.
(Continued)

*Primary Examiner* — Lore R Jarrett
(74) *Attorney, Agent, or Firm* — Troutman Pepper Hamilton Sanders LLP

(57) ABSTRACT

A microfluidic device includes a base comprising a chamber configured to receive a microfluidic component. A sealing member includes a body, an inlet reservoir, and an outlet reservoir, where the inlet reservoir and the outlet reservoir communicate with the chamber through fluid passages when the sealing member and base are removably coupled. A microfluidic component removably within the chamber includes microfluidic channels on a surface thereof and a tissue culture chamber coupled to at least one of the microfluidic channels. The microfluidic channels and the tissue culture chamber are in fluid communication with the inlet and outlet reservoirs through the fluid passages to form a fluid circuit for directing fluid from the inlet reservoir, through the tissue culture chamber, to the outlet reservoir, and from the outlet reservoir back to the inlet reservoir upon tilting the microfluidic device to a forward tilted position and to a reverse tilted position, respectively.

14 Claims, 11 Drawing Sheets

(51) Int. Cl.
*C12M 3/00* (2006.01)
*G01N 33/50* (2006.01)

(56) References Cited

U.S. PATENT DOCUMENTS

| | | |
|---|---|---|
| 6,443,179 B1 | 9/2002 | Benavides et al. |
| 9,944,894 B2 * | 4/2018 | Davis .................... C12M 27/16 |
| 2009/0317793 A1 | 12/2009 | Jonsmann et al. |
| 2012/0135452 A1 | 5/2012 | Shuler et al. |
| 2012/0288911 A1 * | 11/2012 | Matos .................... C12M 25/16 |
| | | 435/174 |
| 2013/0224845 A1 | 8/2013 | Tsao et al. |
| 2014/0021049 A1 | 1/2014 | Joaquim et al. |
| 2015/0219622 A1 * | 8/2015 | Hickman ........... G01N 33/5088 |
| | | 435/29 |

OTHER PUBLICATIONS

PCT International Search Report and Written Opinion corresponding to PCT/US2016/055185, dated Feb. 3, 2017.

* cited by examiner

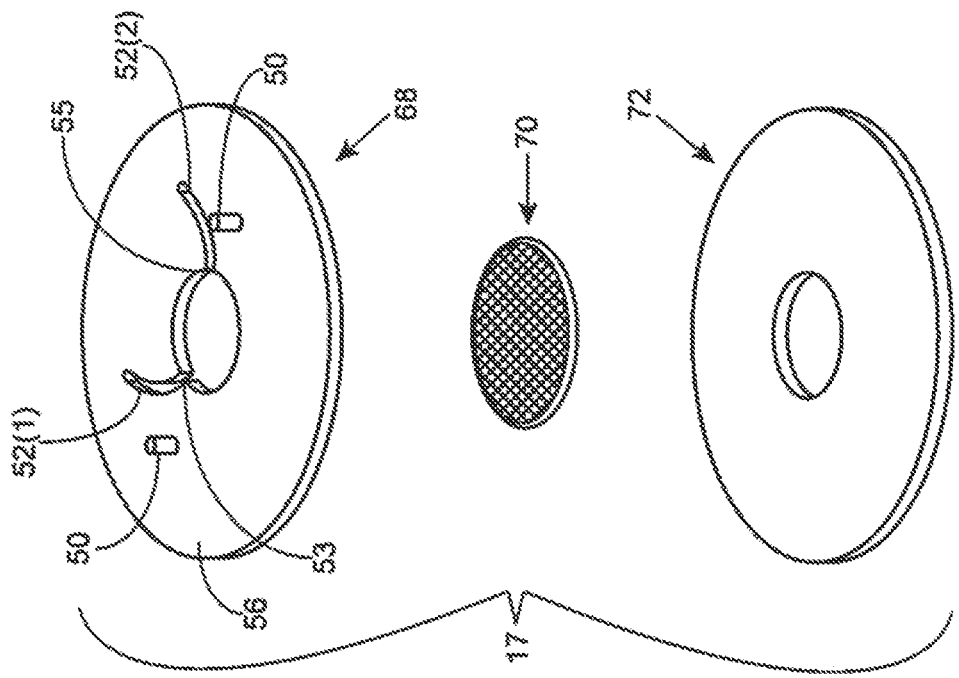
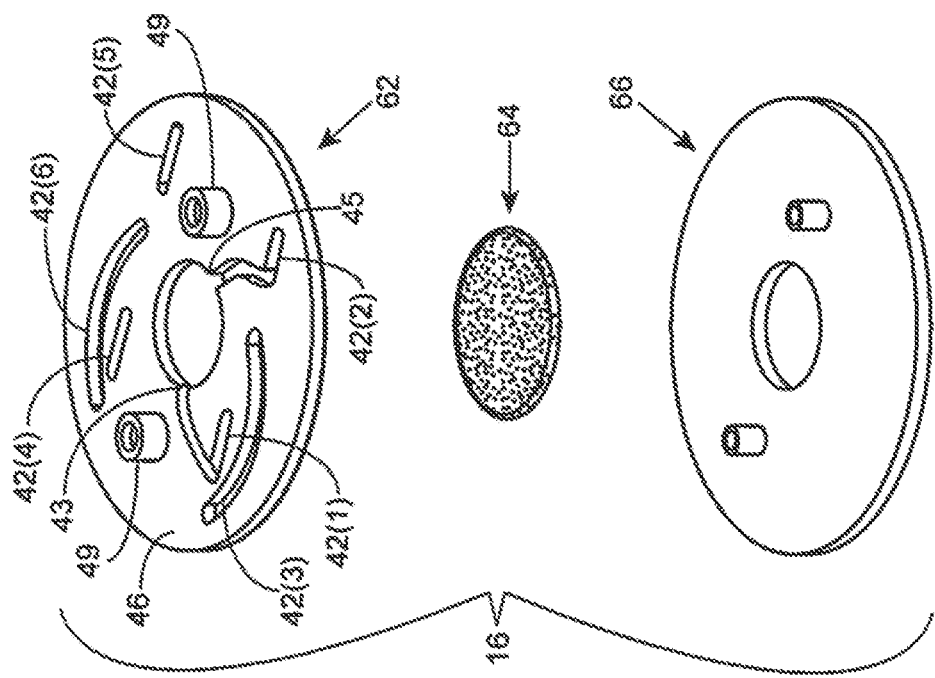

MICROFLUIDIC BODY-ON-A-CHIP DEVICE AND METHODS OF USE THEREOF

This application is a national stage application under 35 U.S.C. § 371 of PCT Application No. PCT/US2016/055185, filed Oct. 3, 2016, which claims the benefit of U.S. Provisional Patent Application Ser. No. 62/235,782, filed Oct. 1, 2015, which is hereby incorporated by reference in its entirety.

GOVERNMENT FUNDING

This invention was made with Government support under Grant awarded by the National Institutes of Health and Grant Number 1106153 awarded by the National Science Foundation. The United States Government has certain rights in the invention.

FIELD OF THE INVENTION

The present invention relates to a microfluidic devices. More specifically, the present invention relates to a microfluidic body-on-a-chip device and methods of use thereof.

BACKGROUND OF THE INVENTION

Animal tests have been invaluable for predicting the potential adverse effects of drugs on humans. It is known, however, that not all drugs that are safe for animals are safe for humans and that only about 10% of drugs that heal diseases in animals do so in humans as well. One of the problems is that animal drug metabolism is not a good mimic of human metabolism.

One alternative to testing drugs is to create the human metabolism from scratch, using in vitro tissues grown from human organs and connecting them with each other via fluidic channels. These complex systems are called multi-organ microphysiological systems, body-on-a-chip systems, or micro cell culture analogs (microCCAs). These microphysiological systems are fluidic cell culture platforms that perfuse several in vitro tissues of human organs with blood surrogate. Cell culture platforms that replicate the size relationships of organs, metabolic activity of tissues, and blood flow in accordance with human physiology, can re-create the human metabolism. Together with physiologically based pharmacokinetic (PBPK) models, such devices have the potential to significantly aid the drug development process.

If operated with human tissues that represent the human body, body-on-a-chip systems could change how new drug candidates are evaluated. Body-on-a-chip systems for drug testing allow for the combination of several tissues with each other, and recirculation of a common cell culture medium among the tissue compartments. Recirculation in a physiologically relevant pattern allows metabolites generated in one tissue chamber to reach all other tissues. Such devices can predict the actions of a drug and also the effects of a drug's metabolites.

Despite their potential usefulness, current body-on-a-chip systems are not yet being used in large-scale drug screening. The predictive power of the devices depends on the authenticity of tissue behavior. The introduction of growth factor reservoirs can help provide unique environments for special tissues that are constructed from primary cells or stem cells. However, many of these systems are operated with pumps and tubing that is expensive and can introduce errors such as those caused by air bubbles and leaking of medium.

Alternatively, devices with gravity driven flow provide a bidirectional flow of fluid, because, once the fluid has passed through the device, the flow needs to be reversed in order to pass over the cell culture again. This creates difficulties for the design of physiologically correct multi-organ body-on-a-chip devices. The main difficulty stems from the fact that all organs have different residence times. A second problem is that some cell types, such as endothelial cells, change their gene expression under bidirectional flow.

Additionally, body-on-a-chip systems need to be sealed to avoid leakage during operation with liquids. There is currently no quick way to provide the necessary sealing of body-on-a-chip systems. The most cost-effective solution to sealing a microfluidic device is to simply stick a PDMS channel face down to a flat surface. Owing to the stickiness of PDMS a nonpermanent seal can be achieved that will allow the flow of liquids at low pressures through the channel. However, this process does not work for any of the other materials, and, in addition to the material constraint, only low pressure liquid flows can be achieved because the sealing is non-permanent and can be broken if high liquid is pumped through the device at higher pressures. In addition, the seal can only be achieved when the devices are dry at the point of assembly. PDMS is also not an ideal material because hydrophobic substances partition into it at a considerable rate, making PDMS devices not useful for drug testing when the drug is hydrophobic.

Sealing microfluidic devices made from other materials can be achieved as well, but those methods involve sealing the devices permanently, and only under dry conditions. If the devices are to be used for cell culture, then such conditions require that cells be introduced and localized to specific regions of the devices after they have been sealed. This has been achieved with photocurable matrixes in which cells can be embedded. However, these matrixes contain cytotoxic components and require the use of UV light and a masking process in order to cure the matrix only where cells should be present in the device. Another method is to introduce the cells via a "supply" channels and direct them with controlled microfluidics (valves and pumps) to their destination in the device.

The present invention is directed to overcoming these and other deficiencies in the art.

SUMMARY OF THE INVENTION

One aspect of the present invention relates to a microfluidic device comprising a base comprising a chamber configured to receive at least one microfluidic component. A sealing member is removably coupled to the base to provide a seal for the chamber. The sealing member includes a body and a first inlet reservoir and a first outlet reservoir, where the first inlet reservoir and the first outlet reservoir are positioned within the body and communicate with the chamber through a first set of fluid passages in the sealing member when the sealing member is coupled to the base. A first microfluidic component is removably within the chamber. The first microfluidic component includes one or more microfluidic channels on a surface thereof and a first tissue culture chamber configured to house a first tissue culture coupled to at least one of the one or more microfluidic channels. When the first microfluidic component is within the chamber, the one or more microfluidic channels and the first tissue culture chamber are positioned in fluid communication with the first inlet reservoir and the first outlet reservoir through the first set of fluid passages in the sealing member to form a first fluid circuit for directing a first flow of fluid from the first inlet reservoir, through the first tissue culture chamber, to the first outlet reservoir, and from the first outlet reservoir back to the first inlet reservoir upon tilting the microfluidic device to a forward tilted position and to a reverse tilted position, with respect to a horizontal axis, respectively.

Another aspect of the present invention relates to a method of delivering a fluid to a tissue culture. This method involves providing the microfluidic device according to the present invention and seeding a first cellular tissue in the first tissue culture chamber of the first microfluidic component. The first microfluidic component with the seeded first tissue culture is inserted into the chamber of the base. The chamber is sealed by reversibly coupling the sealing member to the base. A fluid is provided in the first inlet reservoir and the first outlet reservoir of the sealing member. The fluid is delivered to the first tissue chamber through the first fluid circuit by alternately tilting the microfluidic device between the forward tilted position and the reverse tilted position, with respect to the horizontal axis, respectively.

A further aspect of the invention relates to a method of delivering a fluid to a cellular tissue. This method involves seeding a first cellular tissue in a first tissue culture chamber of a first microfluidic component comprising one or more microfluidic channels on a surface thereof and a first tissue culture chamber configured to house the first cellular tissue coupled to at least one of the one or more microfluidic channels. The first microfluidic component with the seeded first tissue culture is inserted into a microfluidic device and the microfluidic device is sealed. A fluid is provided in a first inlet reservoir and a first outlet reservoir of the microfluidic device. The one or more microfluidic channels and the first tissue culture chamber are positioned in fluid communication with the first inlet reservoir and the first outlet reservoir through a first set of fluid passages to form a first fluid circuit. The fluid is delivered to the first tissue chamber through the first fluid circuit of the microfluidic device by alternately tilting the microfluidic device between a forward tilted position and a reverse tilted position, with respect to a horizontal axis of the microfluidic device, respectively.

Yet another aspect of the present invention relates a method of simulating human metabolism in a microfluidic device. This method involves seeding a GI tract tissue in a first tissue culture chamber of a first microfluidic component comprising one or more microfluidic channels on a surface thereof and a first tissue culture chamber configured to house the first cellular tissue coupled to at least one of the one or more microfluidic channels. A liver tissue is seeded in the second tissue culture chamber of a second microfluidic component comprising another one or more microfluidic channels on a surface thereof and a second tissue culture chamber configured to house a second tissue culture coupled to at least one of the another one or more microfluidic channels. The first microfluidic component with the seeded GI tract tissue and the second microfluidic component with the seeded liver tissue are inserted into the microfluidic device in a stacked arrangement and the microfluidic device is sealed. A fluid is provided in a first inlet reservoir and a first outlet reservoir of the microfluidic device. The one or more microfluidic channels and the first tissue culture chamber are positioned in fluid communication with the first inlet reservoir and the first outlet reservoir through a first set of fluid passages to form a first fluid circuit. The fluid is provided in a second inlet reservoir and a second outlet reservoir of the microfluidic device. The another one or more microfluidic channels and the second tissue culture chamber are positioned in fluid communication with the second inlet reservoir and the second outlet reservoir through a second set of fluid passages to form a second fluid circuit. The fluid is delivered to the first tissue chamber through the first fluid circuit of the microfluidic device and to the second tissue chamber through the second fluid circuit by alternately tilting the microfluidic device between a forward tilted position and a reverse tilted position, with respect to a horizontal axis of the microfluidic device, respectively.

Another aspect of the present invention relates to a method for determining a pharmacokinetic, a pharmacodynamic, or a pharmacokinetic-pharmacodynamic (PKPD) effect of an agent on a cellular tissue. This method involves providing the microfluidic device according to the present invention and seeding the cellular tissue in the first tissue culture chamber of the first microfluidic component. The first microfluidic component with the seeded first tissue culture is inserted into the chamber of the base. The chamber is sealed by reversibly coupling the sealing member to the base. A fluid comprising the agent is provided in the first inlet reservoir and the first outlet reservoir of the sealing member. The fluid comprising the agent is delivered to the first tissue chamber through the first fluid circuit by alternately tilting the microfluidic device between the forward tilted position and the reverse tilted position, with respect to the horizontal axis, respectively. A pharmacokinetic, a pharmacodynamic, or a pharmacokinetic-pharmacodynamic assay is performed on the cellular tissue after the delivering. One or more in vitro pharmacokinetic or pharmacodynamic effects of the agent on the cellular tissue are determined based on the assay.

The microfluidic device of the present invention provides a low-cost microfluidic body-on-a-chip platform that replicates the relationship between body tissue and blood volume of the human body in a scaled down, under a near-physiologic condition. The microfluidic device of the present invention advantageously provides: 1) a modular design that allows the user to mature tissues independent of each other, and to later add additional tissues to the system using different chips; 2) rendering the bidirectional fluidic flow generated on a rocking platform unidirectional, such as by the use of a passive value; and 3) a closing mechanism that allows for a rapid, leak-free, and air bubble-free assembly of the device, and also permits opening of the device without loss of tissue properties so that tissues can be analyzed at the end of the experiment. The device allows for recirculating, unidirectional flow without the use of moving parts, such as a pump. The device of the present invention therefore presents a low-cost approach to culturing multiple tissue of primary human origin under a near-physiologic condition within one body-on-a-chip platform. The device of the present invention allows any number of chip platforms to be utilized, and, by way of example, more than two chips may be employed to mimic physiological systems in combination.

BRIEF DESCRIPTION OF THE DRAWINGS

FIG. 4A is an exploded view of the first microfluidic component of FIG. 1B.

FIG. 4B is an exploded view of the second microfluidic component of FIG. 1B.

DETAILED DESCRIPTION OF THE INVENTION

The present invention relates to a microfluidic devices. More specifically, the present invention relates to a microfluidic body-on-a-chip device and methods of use thereof.

One aspect of the present invention relates to a microfluidic device comprising a base comprising a chamber configured to receive at least one microfluidic component. A sealing member is removably coupled to the base to provide a seal for the chamber. The sealing member includes a body and a first inlet reservoir and a first outlet reservoir, where the first inlet reservoir and the first outlet reservoir are positioned within the body and communicate with the chamber through a first set of fluid passages in the sealing member when the sealing member is coupled to the base. A first microfluidic component is removably within the chamber. The first microfluidic component includes one or more microfluidic channels on a surface thereof and a first tissue culture chamber configured to house a first tissue culture coupled to at least one of the one or more microfluidic channels. When the first microfluidic component is within the chamber, the one or more microfluidic channels and the first tissue culture chamber are positioned in fluid communication with the first inlet reservoir and the first outlet reservoir through the first set of fluid passages in the sealing member to form a first fluid circuit for directing a first flow of fluid from the first inlet reservoir, through the first tissue culture chamber, to the first outlet reservoir, and from the first outlet reservoir back to the first inlet reservoir upon tilting the microfluidic device to a forward tilted position and to a reverse tilted position, with respect to a horizontal axis, respectively.

Figure 1A:
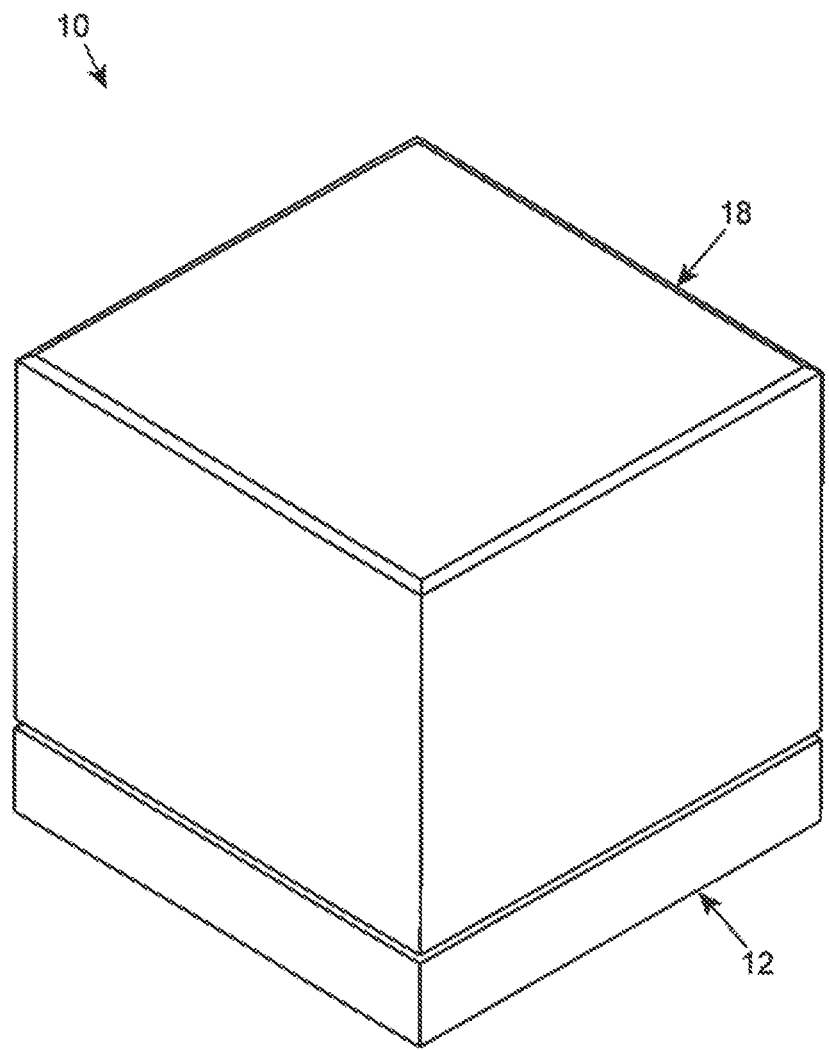
FIG. 1A is an assembled perspective view of a first embodiment of a microfluidic device of the present invention.
Figure 1B:
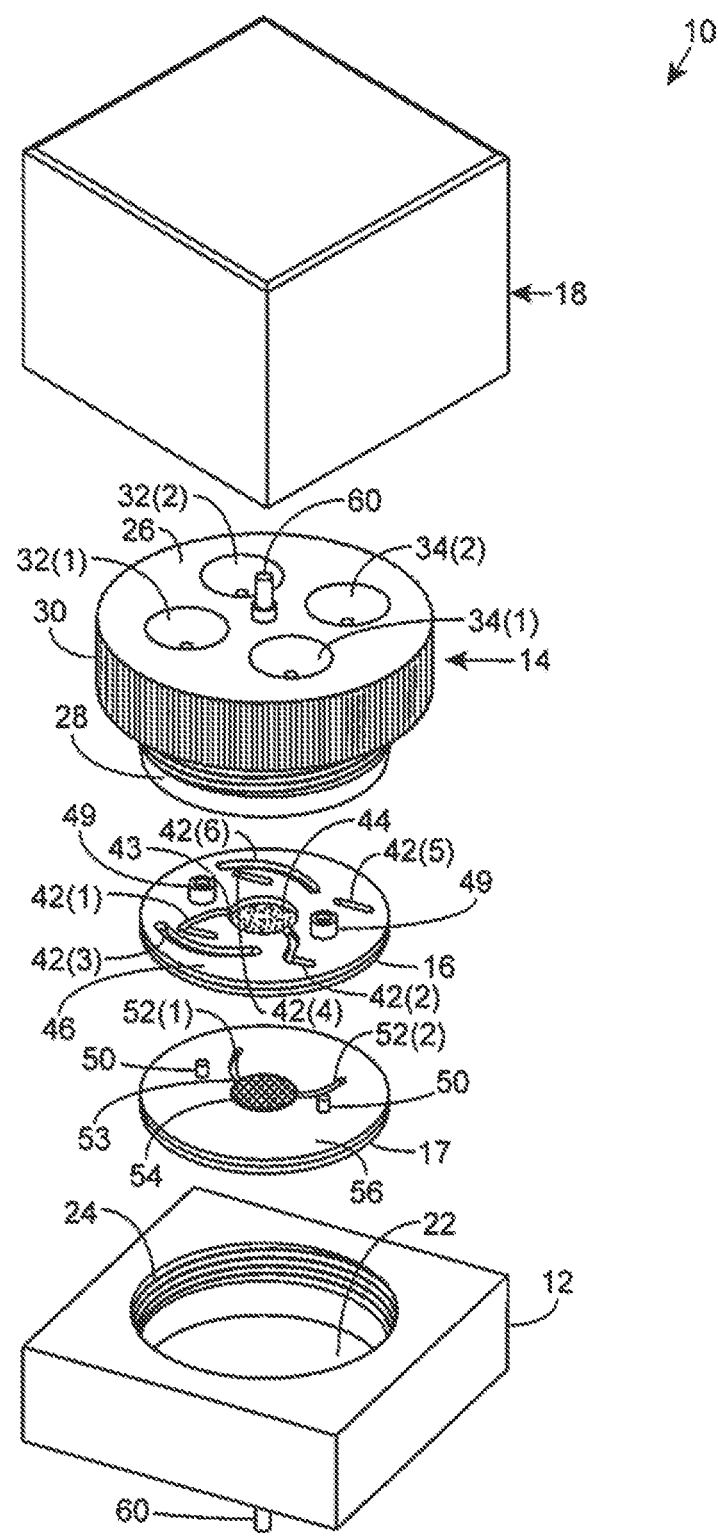
FIG. 1B is an exploded perspective view of the first embodiment of the microfluidic device of FIG. 1A.

FIGS. 1A and 1B are assembled and exploded perspective views of a first embodiment of microfluidic device 10 of the present invention. Microfluidic device 10 includes base 12, sealing member 14, first microfluidic component 16, optional second microfluidic component 17, and lid 18, although microfluidic device 10 may include other types or numbers of elements or components, such as additional microfluidic components, in other combinations. The elements of microfluidic device 10, as described above, are formed from one of polydimethylsiloxane, plastic, or silicon, although other suitable materials may be utilized. According to one embodiment, the elements of microfluidic device 10 are formed using 3-D printing, although the elements of microfluidic device 10 may be formed using other methods, such as injection molding.

Base 12 includes chamber 22 sized to allow at least first microfluidic component 16 to be removably inserted therein. However, chamber 22 may be sized to receive additional elements, such as second microfluidic component 17. Although first microfluidic component 16 and second microfluidic component 17 are described, chamber 22 may be sized to receive any number of microfluidic components in combination. Although base 12 is described as having single chamber 22, in another embodiment, base 12 could be configured like to a well plate having any number of chambers located therein to receive and house microfluidic components or chips. Base 12 further includes threaded portion 24 on an interior surface of chamber 22 that allows base 12 to be removably coupled to a corresponding threaded portion of sealing member 14 as discussed below. Base 12 is shown as having a square configuration. However, base 12 may have any other shapes such as circular or rectangular, by way of example only.

Sealing member 14 includes body 26 including threaded stem 28 and top portion 30. Threaded stem 28 is sized to be inserted into chamber 22 of base 12 and to interact with threaded portion 24 in chamber 22 as a threaded screw to removably couple sealing member 14 to base 12. Sealing member 14 provides a seal with base 12 like a gasket around the outer edges of threaded stem 28 for chamber 22. According to one embodiment, sealing member 14 provides a bubble-free and leak-free closure that may be utilized even when one or more elements of microfluidic device 10 are in a wet condition.

Figure 2A:
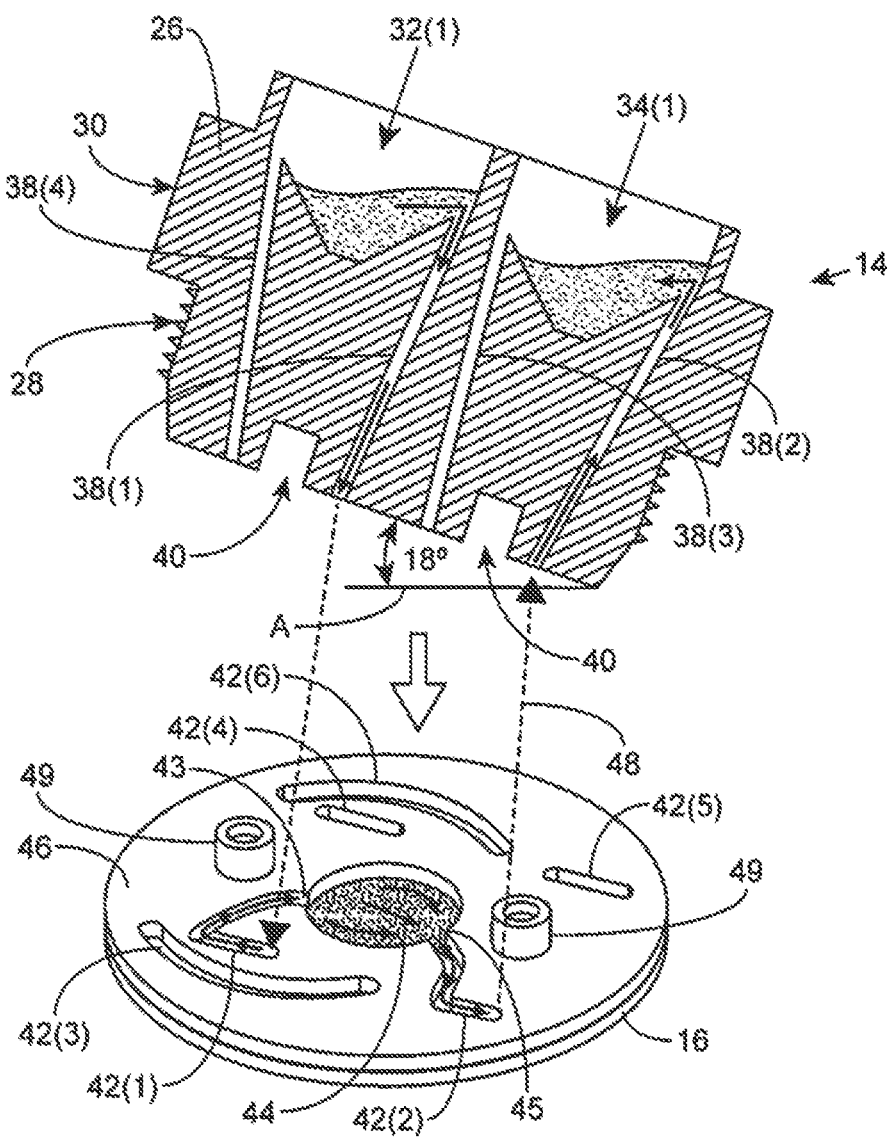
FIGS. 2A and 2B are exploded views of the sealing member and the first microfluidic component of FIG. 1B with the sealing member (shown in cross-section) in a forwarded titled orientation (FIG. 2A) and a reverse titled orientation (FIG. 2B).
Figure 2B:
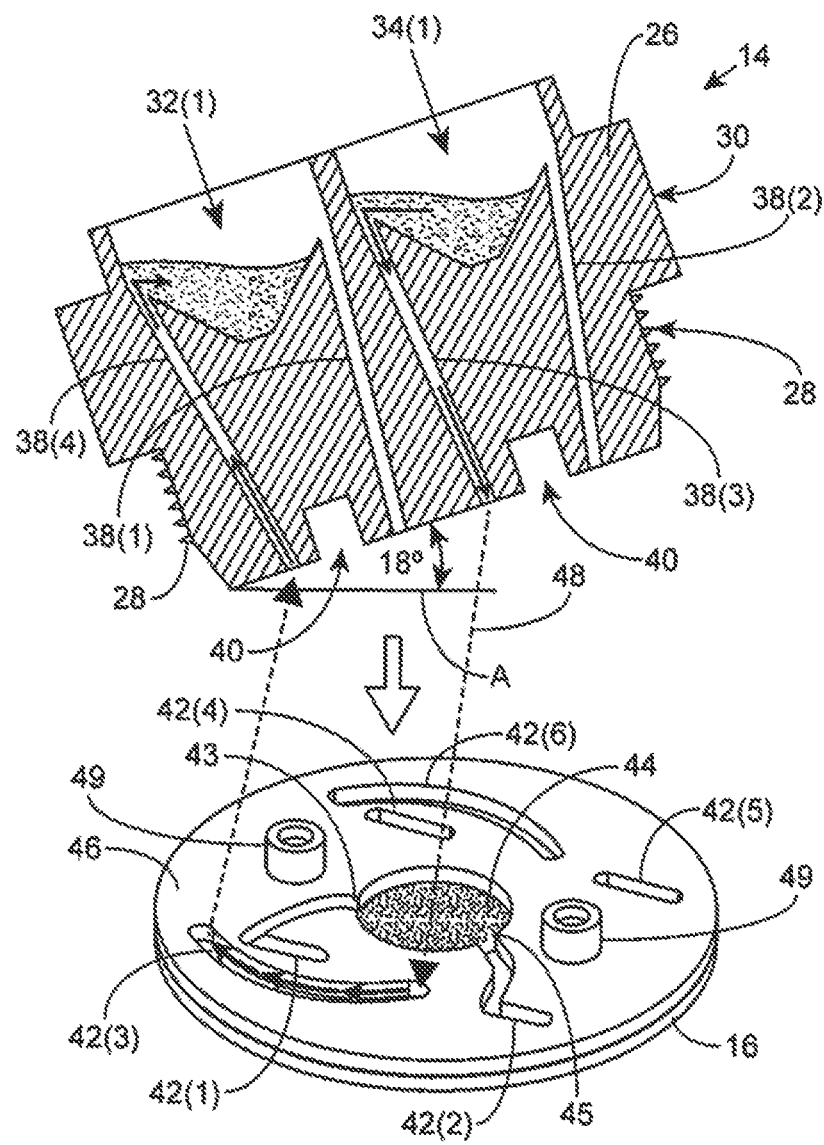

Sealing member 14 further includes first and second inlet reservoirs 32(1) and 32(2), respectively, and first and second outlet reservoirs 34(1) and 34(2), respectively, positioned within top portion 30 of body 26. First inlet reservoir 32(1) and first outlet reservoir 34(1) are in fluid communication with chamber 22 through first set of fluid passages 38(1)-38(4), as shown in FIGS. 2A and 2B, when sealing member 14 is coupled to base 12. Sealing member 14 also includes alignment holes 40 in order to align first microfluidic component 16 with first set of fluid passages 38(1)-38(4) as described in further detail below.

Figure 3A:
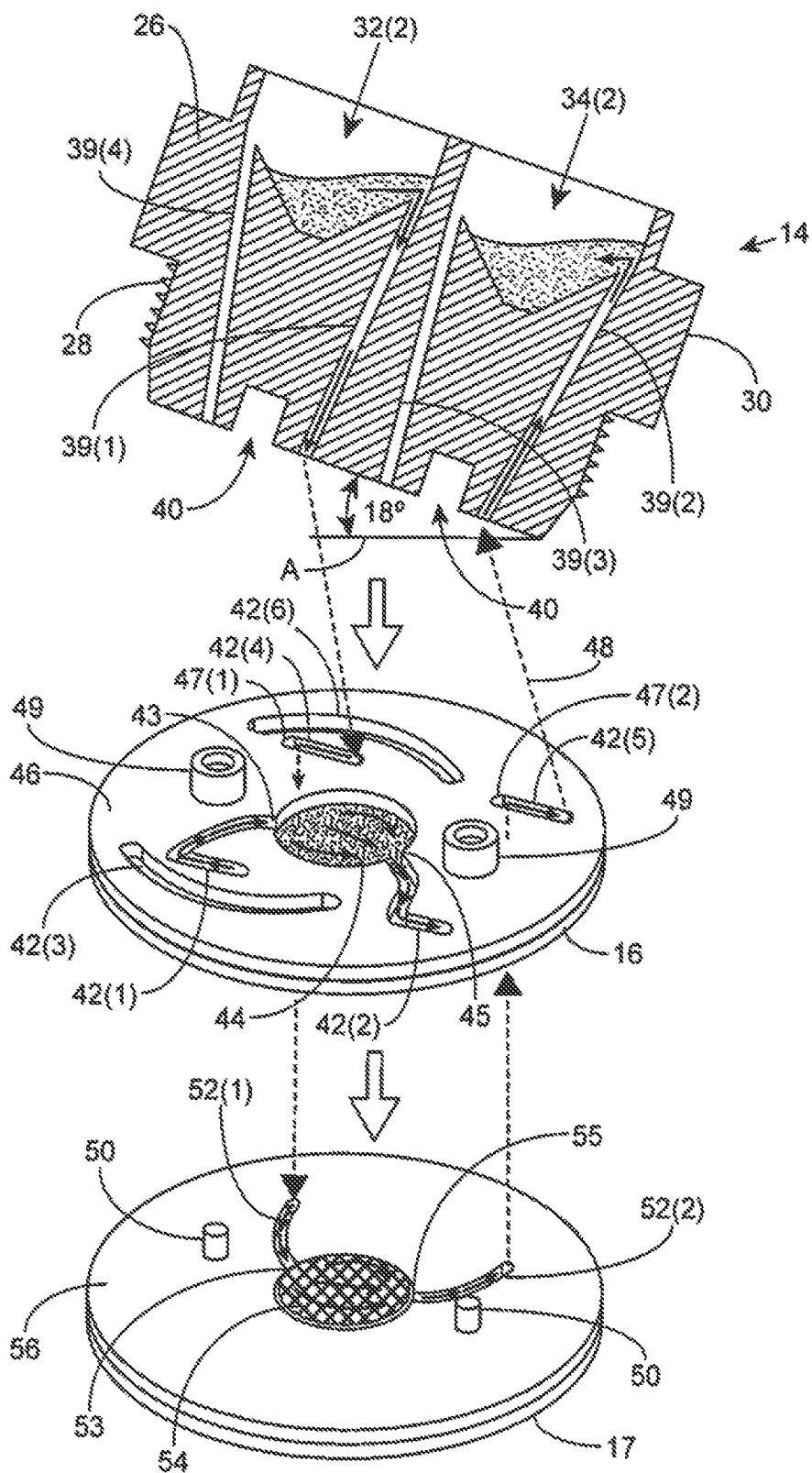
FIGS. 3A and 3B are exploded views of the sealing member, the first microfluidic component, and the second microfluidic component of FIG. 1B in with the sealing member (shown in cross-section) in a forwarded titled orientation (FIG. 3A) and a reverse titled orientation (FIG. 3B).
Figure 3B:
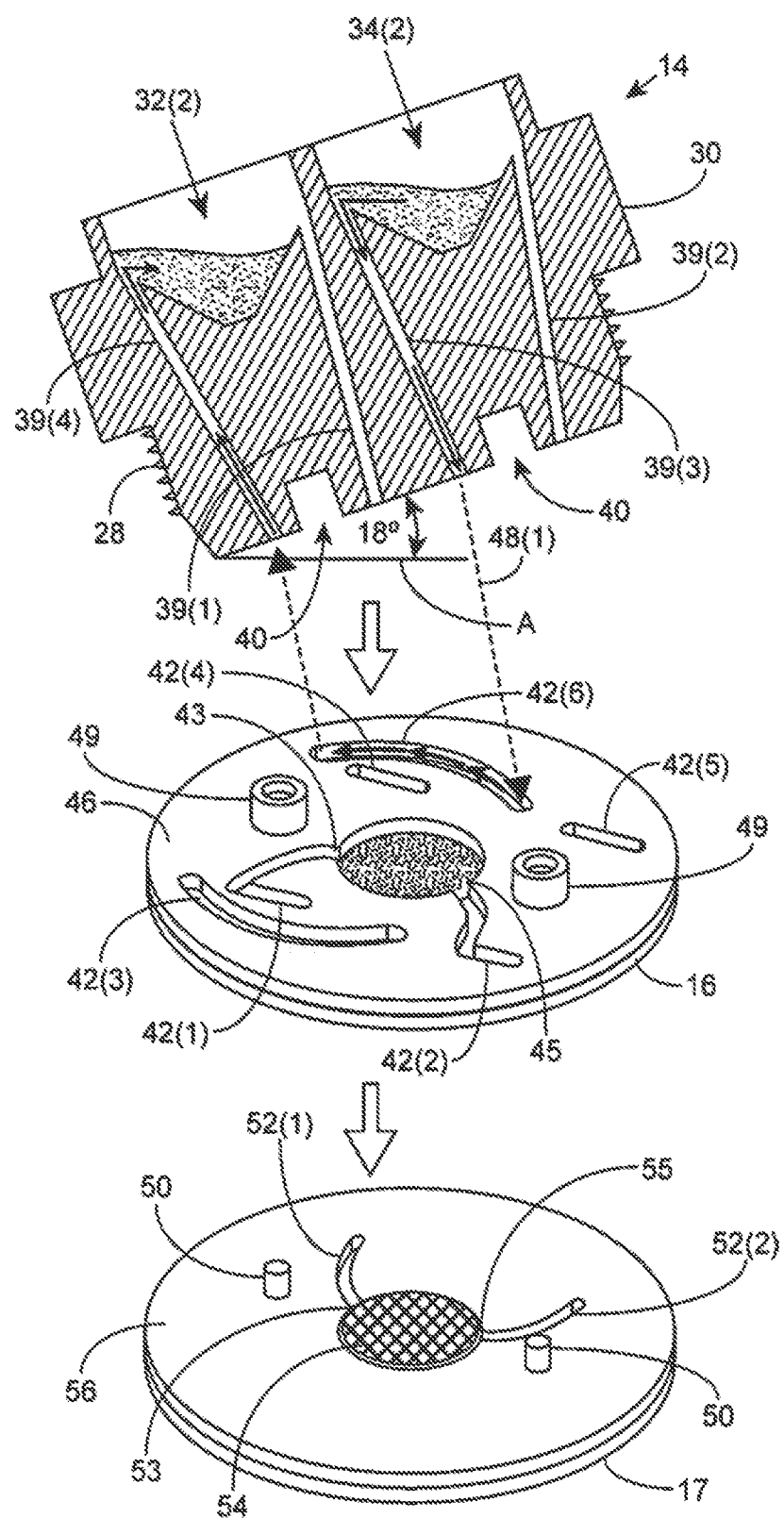

According to one embodiment, second inlet reservoir 32(2) and second outlet reservoir 34(2) are also in fluid communication with chamber 22 through second set of fluid passages 39(1)-39(4), as shown in FIGS. 3A and 3B, when sealing member 14 is coupled to base 12. First set of fluid passages 38(1)-38(4) and second set of fluid passages 39(1)-

39(4) are sized as capillary channels with dimensions suitable to prevent backflow of fluid through one of the fluid passages while forward flow occurs in another due to capillary forces as described in greater detail below. Sealing member 14 also includes alignment holes 40 in order to align first microfluidic component 16 with first set of fluid passages 38(1)-38(4) as described in further detail below.

First microfluidic component 16 is configured to be removably inserted into chamber 22. According to one embodiment, first microfluidic component 16 includes microfluidic channels 42(1)-42(3) and first tissue culture chamber 44 located on surface 46, although first microfluidic component may include additional microfluidic channels, such as optional microfluidic channels 42(4)-42(6) as described below, or additional tissue culture chambers in series or in parallel with tissue culture chamber 44. In one embodiment, microfluidic channels 42(1)-42(6) have a width of about 5 µm to about 5 mm.

First tissue culture chamber 44 is coupled to microfluidic channel 42(1) at a first end 43 of tissue culture chamber 44 and microfluidic channel 42(2) at second end 45 of tissue culture chamber 44 located opposite first end 43, to provide a fluid communication path from microfluidic channel 42(1) through tissue culture chamber 44 to microfluidic channel 42(2). Microfluidic channel 42(3) is located separately on surface 46 from microfluidic channels 42(1) and 42(2) and not in fluid communication with first tissue culture chamber 44. Microfluidic channels 42(4)-42(6) are optional and are only utilized when first microfluidic component 16 is utilized in combination with second microfluidic component 17 as described below. Microfluidic channel 42(4) includes first hole 47(1), while microfluidic channel 42(6) includes second hole 47(2), to provide fluid communication through first microfluidic component 16 to second microfluidic component 17. Microfluidic channel 42(6) is located separately from microfluidic channels 42(4) and 42(5) and is not in fluid communication with the second microfluidic component 17.

First tissue culture chamber 44 is configured to house a cellular tissue, such as liver tissue, kidney tissue, gastrointestinal tract tissue, lung tissue, skin tissue, brain tissue, or heart tissue, by way of example. First tissue culture chamber 44 may include a porous membrane or 3-D scaffold located within first tissue culture chamber 44 for seeding the cellular tissue as described in further detail below.

When first microfluidic component 16 is positioned within chamber 22, microfluidic channels 42(1)-42(3) and first tissue culture chamber 44 are positioned in fluid communication with first inlet reservoir 32(1) and first outlet reservoir 34(1) through first set of fluid passages 38(1)-38(4) in sealing member 14 to form first fluid circuit 48, as illustrated in FIGS. 2A and 2B. First fluid circuit 48 extends from first inlet reservoir 32(1), through fluid passage 38(1) into microfluidic channel 42(1), through first tissue culture chamber 44, into microfluidic channel 42(2), through fluid passage 38(2) to first outlet reservoir 34(1), and back from first outlet reservoir 34(1), through fluid passage 38(3) to microfluidic channel 42(3), and through fluid passage 38(4) to first inlet reservoir 32(1). First microfluidic component 16 includes alignment members 49 positioned on surface 46 and configured to mate with alignment holes 40 of sealing member 14 in order to provide proper alignment of the elements of first fluid circuit 48.

First fluid circuit 48 is configured so that the flow of fluid as delivered by gravity to first tissue chamber 44 from first fluid circuit 48 is unidirectional when microfluidic device 10 is moving between the forward tilted and reverse tilted positions. First fluid circuit 48 further has dimensions configured to provide a flow rate of the flow of fluid delivered to first tissue culture chamber 44 substantially similar to a physiological flow rate in an organ, such as a liver or a GI tract, by way of example only. The operability of first fluid circuit 48 when microfluidic device 10 is tilted between a forward tilted position (FIG. 2A) and a reverse tilted position (FIG. 2B) is described in detail below. Although a tilt angle of plus or minus 18 degrees is illustrated, it is to be understood that other tilt angles could be utilized.

The hydrostatic pressure drop between first inlet reservoir 32(1) and first outlet reservoir 34(1) at a platform tilt angle with respect to horizontal axis A of microfluidic device 10 may be utilized to determine the hydraulic resistances that are needed to achieve near physiologic flow rates within fluid circuit 48. The hydrostatic pressure drop may also be utilized to determine the length, width, and depth of first set of fluid passages 38(1)-38(4) that will provide the needed hydraulic resistance to calculate dimensions for microfluidic channels 42(1)-42(3) of first microfluidic component 16. The hydrostatic pressure drop is given by equation (1):

$$\Delta P = \rho g h \text{ [Pa]}, \tag{1}$$

with ΔP being the pressure drop between first inlet reservoir 32(1) and first outlet reservoir 34(1) for a height difference h at a given tilting angle of microfluidic device 10 with respect to horizontal axis A, with ρ being the density of fluid or cell culture medium in kg mm$^3$, and g being the gravity constant. The hydraulic resistance is then calculated based on a desired physiological flow rate using equation (2):

$$R = \Delta P / Q(\text{organ segment}) \text{ [(Pa×s)/m}^3\text{]}, \tag{2}$$

with R being the hydraulic resistance of the components of fluid circuit 48 that unidirectionally deliver fluid to first tissue chamber 44, i.e. microfluidic channels 42(1) and 42(2) plus tissue chamber 44 and Q(organ, scaled) being the flow rate through 1/95 000 of the organ. Given the hydrostatic pressure drop that occurs at a tilting angle, the sum of the hydraulic resistances present in first fluid circuit 48 including first cell culture chamber 44, microfluidic channels 42(1) and 42(2) and fluid passages 38(1) and 38(3) determine the flow rate across first tissue chamber 44 as given by equation (3):

$$Q(\text{organ, segment}) = \rho g h / (R(\text{microfluidic channel } 42(1)) + R(\text{first tissue chamber } 44) + R(\text{microfluidic channel } 42(2)) + R(\text{fluid passages } 38(1) \text{ and } 38(3)) \text{ [L min}^{-1}\text{]} \tag{3}$$

Since ΔP is determined by the density of the fluid or cell culture medium and the platform tilt angle according to equation (1), the hydraulic resistance of first tissue culture chamber 44 is given by its size, and the hydraulic resistance of the valve is given by the dimensions of the valve, one way to achieve the needed fluid flow rate is by adjusting the height, width and length of microfluidic channel 42(1) that supplies the first tissue culture chamber 44 with medium as given by equation (4).

$$R(\text{channels}) = [12 \eta L / (1 - 0.63(h/w))] \times (1/h^3 w) \tag{4}$$

with η being the dynamic viscosity of the fluid or cell culture medium, L being the length of microfluidic channel 42(1), h being the height of microfluidic channel 42(1), and w being the width of microfluidic channel 42(1) (with w>h for all channels). In one embodiment, kept microfluidic channel lengths and heights may be held constant for each chip and the microfluidic channel widths may be varied to achieve the needed hydraulic resistance. In one example, the width of the all microfluidic channels is greater than the height. Since liquid levels in each of the inlet and outlet reservoirs change over time (i.e., Δh changes over time), and the platform is tilted back and forth at time intervals, such as 60 seconds (i.e. not enough time for Δh to become zero), the flow rate does not reach steady state.

Second microfluidic component 17 is also configured to be removably inserted into chamber 22. According to one embodiment, second microfluidic component 17 is inserted into chamber 22 in a stacked arrangement with first microfluidic component 16. Second microfluidic component 17 includes alignment members 50 configured to mate with alignment members 49 of first microfluidic component 16 in order to provide proper alignment of first microfluidic component 16 and second microfluidic component 17 in the stacked arrangement. Second microfluidic component 17 includes microfluidic channels 52(1) and 52(2) and second tissue culture chamber 54 located on surface 56 thereof. In one embodiment, microfluidic channels 52(1) and 52(2) have a width of about 5 µm to about 5 mm. Second tissue culture chamber 54 is coupled to microfluidic channel 52(1) at first end 53 of second tissue culture chamber 54 and microfluidic channel 52(2) at second end 55 of second tissue culture chamber 54 located opposite first end 53.

Second tissue culture chamber 54 is configured to house a cellular tissue, such as liver tissue, kidney tissue, gastrointestinal tract tissue, lung tissue, skin tissue, brain tissue, or heart tissue, by way of example. Second tissue culture chamber 54 may include a porous membrane or 3-D scaffold located within second tissue culture chamber 54 for seeding the cellular tissue as described in further detail below.

When first microfluidic component 16 and second microfluidic component 17 are positioned within chamber 22 in a stacked arrangement, microfluidic channels 42(4)-42(6) in first microfluidic component 16, microfluidic channels 52(1) and 52(2) in second microfluidic component 17, and second tissue culture chamber 54 are positioned in fluid communication with second inlet reservoir 32(2) and second outlet reservoir 34(2) through second set of fluid passages 39(1)-39(4) in sealing member 14 to form second fluid circuit 58, as illustrated in FIGS. 3A and 3B. Second fluid circuit 58 extends from second inlet reservoir 32(2), through fluid passage 39(1) into microfluidic channel 42(4), through hole 47(1) to microfluidic channel 52(1), through second tissue culture chamber 54 into microfluidic channel 52(2), through hole 47(2) into microfluidic channel 42(5), through fluid passage 39(2) to second outlet reservoir 34(2), and back from second outlet reservoir 34(2), through fluid passage 39(3) to microfluidic channel 42(6), and through fluid passage 39(4) to second inlet reservoir 32(2). Alignment members 50 positioned on surface 56 of the second microfluidic component 17 and alignment members 4 of first microfluidic component 16 couple to provide proper alignment of the elements of second fluid circuit 58.

Second fluid circuit 58 is configured so that the flow of fluid as delivered by gravity to second tissue culture chamber 54 from second fluid circuit 58 is unidirectional when microfluidic device 10 is moving between the forward tilted and reverse tilted positions. Second fluid circuit 48 has dimensions configured to provide a flow rate of the flow of fluid delivered to second tissue culture chamber 54 substantially similar to a physiological flow rate in an organ, such as a liver or a GI tract, by way of example only. The operability of second fluid circuit 58 when microfluidic device 10 is tilted between a forward tilted position (FIG. 3A) and a reverse tilted position (FIG. 3B) is described in detail below. Although a tilt angle of plus or minus 18 degrees is illustrated, it is to be understood that other tilt angles could be utilized.

The hydrostatic pressure drop between second inlet reservoir 32(2) and second outlet reservoir 34(2) at a platform tilt angle with respect to horizontal axis A of microfluidic device 10 may be utilized to determine the hydraulic resistances that are needed to achieve near physiologic flow rates within second fluid circuit 58 in the same manner as described above with respect to first fluid circuit 48.

Turning now to FIGS. 4A and 4B, according to one embodiment, first microfluidic component 16 and second microfluidic component 17 are separately assembled to allow separate seeding of cellular tissues as described in detail below. First microfluidic component 16 includes surface chip 62, porous membrane 64, and support chip 66, which may be assembled together using a biocompatible adhesive. Surface chip 62 includes surface 46 with microfluidic channels 42(1)-42(6) and first tissue culture chamber 44 thereon, by way of example. According to one embodiment, porous membrane 64 is a porous polycarbonate membrane, such as catalog #P/N PCT45025100 produced by Sterlitech Corp., Kent, Wash. Porous membrane 64 is sandwiched between surface chip 62 and support chip 66.

Second microfluidic component 17 includes surface chip 68, porous membrane 70, and support chip 72, which may be assembled together using a biocompatible adhesive. Surface chip 68 includes surface 56 with microfluidic channels 52(1) and 52(2) and second tissue culture chamber 54 thereon, by way of example. According to one embodiment, porous membrane 70 is a porous polycarbonate membrane, such as catalog #P/N PCT45025100 produced by Sterlitech Corp., Kent, Wash. Porous membrane 70 is sandwiched between surface chip 68 and support chip 72. According to one embodiment, cell tissues may be seeded directly on porous membranes 64 and 72, which support tissue growth thereon. Alternatively, a woven nylon scaffold may be inserted above porous membranes 64 and/or 72 to provide a 3D culture environment for the tissue. Referring again to FIGS. 1A and 1B, lid 18 may be utilized to further seal microfluidic device 10 prior to tilting as described below.

Figure 5:
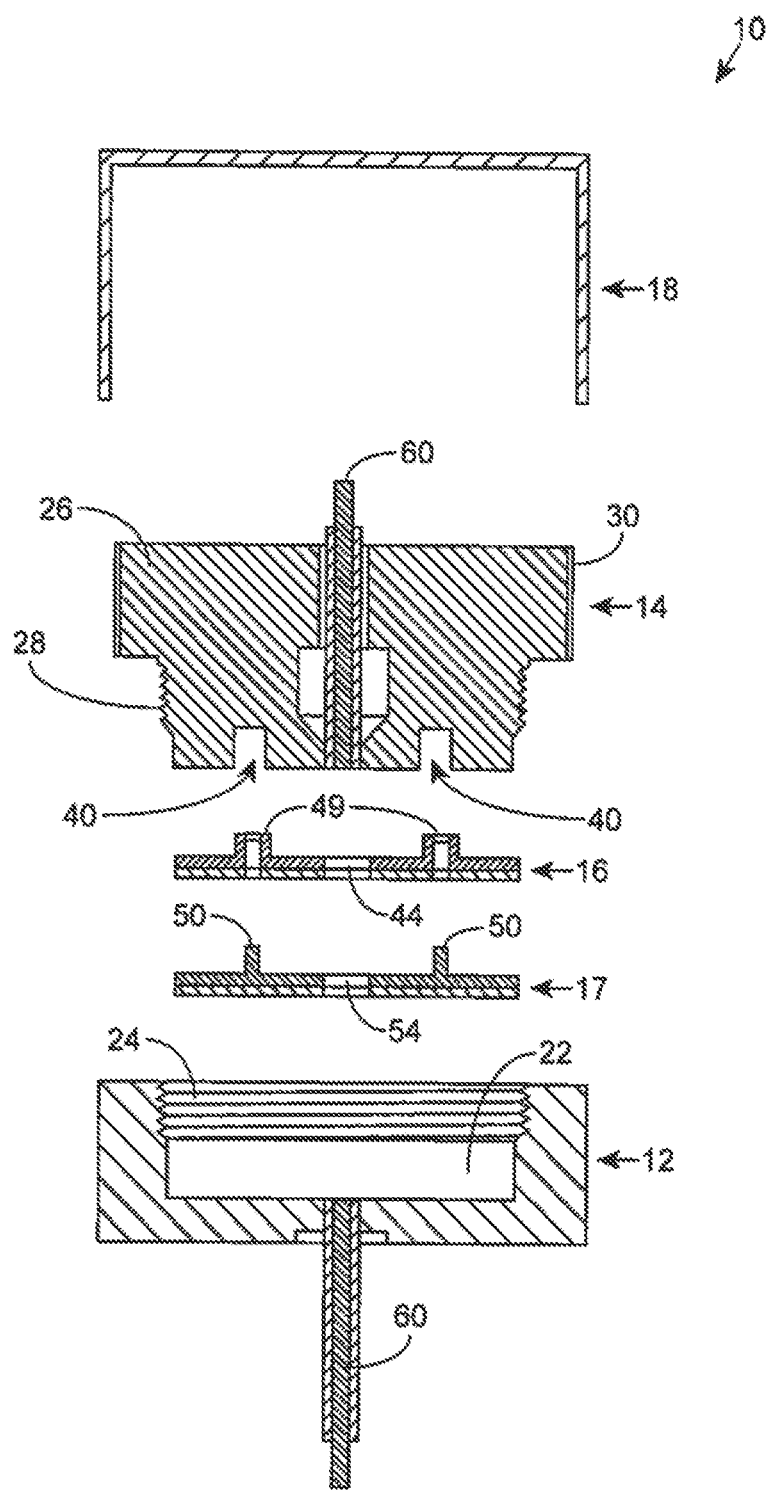
FIG. 5 is a side cross-sectional exploded view of the microfluidic device of FIG. 1B.

Turning now to FIG. 5, according to one embodiment, base 12 and sealing member 14 both include electrodes 60 located therein. Electrodes 60 are positioned to provide a current across chamber 22. According to one embodiment, electrodes 60 are Ag/AgCl electrodes constructed from 3 mm thick, hollow silver tubes and silver chloride electrodes.

Another aspect of the present invention relates to a method of delivering a fluid to a tissue culture. This method involves providing the microfluidic device according to the present invention and seeding a first cellular tissue in the first tissue culture chamber of the first microfluidic component. The first microfluidic component with the seeded first tissue culture is inserted into the chamber of the base. The chamber is sealed by reversibly coupling the sealing member to the base. A fluid is provided in the first inlet reservoir and the first outlet reservoir of the sealing member. The fluid is delivered to the first tissue chamber through the first fluid circuit by alternately tilting the microfluidic device between the forward tilted position and the reverse tilted position, with respect to the horizontal axis, respectively.

First, microfluidic device 10 according to the present invention is provided. Microfluidic device 10 may be provided with first microfluidic component 16 and second microfluidic component 17, by way of example, although other numbers of microfluidic components may be provided, or first microfluidic component 16 alone may be utilized.

According to one embodiment, first microfluidic component 16 and second microfluidic component 17 are configured to form first fluid circuit 48 and second fluid circuit 58 when inserted into chamber 22 of base 12. First fluid circuit 48 and second fluid circuit 58 have dimensions configured to provide a flow rate of the flow of fluid delivered to first tissue chamber 44 and second tissue culture chamber 54, respectively, substantially similar to a physiological flow rate in an organ, such as a liver or a GI tract, as described in greater detail above.

Next, a first cellular tissue is seeded in first tissue culture 44 chamber of first microfluidic component 16. The first cellular tissue is seeded directly on porous membrane 64, which is located between surface chip 62 and support chip 66 and supports tissue growth thereon. Alternatively, a woven nylon scaffold may be inserted above porous membrane 64 to provide a 3D culture environment for the tissue. The tissue is seeded with first microfluidic component 16 located outside of base 12 of microfluidic device 10. The first microfluidic component 16 may then be placed in a petri dish for a period of days to allow for cellular growth on porous member 64. The first cellular tissue may be liver tissue, kidney tissue, gastrointestinal tract tissue, lung tissue, skin tissue, brain tissue, or heart tissue, by way of example.

According to one embodiment, a second cellular tissue is also seeded in second tissue culture 54 chamber of second microfluidic component 17. The second cellular tissue is seeded directly on porous membrane 70, which is located between surface chip 68 and support chip 72 and supports tissue growth thereon. Alternatively, a woven nylon scaffold may be inserted above porous membrane 70 to provide a 3D culture environment for the tissue. The tissue is seeded with second microfluidic component 17 located outside of base 12 of microfluidic device 10. The second microfluidic component 17 may then be placed in a petri dish for a period of days to allow for cellular growth on porous member 70. The second cellular tissue may be kidney tissue, gastrointestinal tract tissue, lung tissue, skin tissue, brain tissue, or heart tissue, by way of example. The modularity of first microfluidic component 16 and second microfluidic component 17 allows different tissues having different growth periods to be developed separately and then utilized with microfluidic device 10.

In the next method step, first microfluidic component 16 with the seeded first tissue culture is inserted into chamber 22 of base 12. Alignment members 49 are mated with alignment holes 40 of sealing member 14 in order to provide proper alignment of the elements of first fluid circuit 48 after insertion of first microfluidic component. First microfluidic component 16 may be inserted alone into chamber 22 or in combination with second microfluidic component 17 in a stacked arrangement to form second fluid circuit 58.

Next, chamber 22 is sealed by reversibly coupling sealing member 14 to base 12. Threaded stem 28 of sealing member 14 is inserted into chamber 22 of base 12 and turned as a threaded screw interacting with threaded portion 24 in base 12 to removably couple sealing member 14 to base 12. Sealing member 14 provides a seal like a gasket with base 12 around the outer edges of threaded stem 28 for chamber 22. According to one embodiment, sealing member 14 provides a bubble-free and leak-free closure that may be utilized even when one or more elements of microfluidic device 10 are in a wet condition.

Next, a fluid or cell culture medium is provided in first inlet reservoir 32(1) and first outlet reservoir 34(1) of sealing member 14. The fluid may also be provided in second inlet reservoir 32(2) and second outlet reservoir 34(2) when second microfluidic component 17 is also utilized.

According to one embodiment, the fluid is a blood surrogate selected from the group consisting of hemoglobin-based oxygen carriers, such as stroma-free hemoglobin, chemically crosslinked hemoglobin, polymerized hemoglobin, polymer conjugated hemoglobin, encapsulated hemoglobin, and perfluorocarbon-based oxygen carriers, such as perfluoroalkyl ethers, perfluoro crown ethers such as perfluoro-15-crown-5-ether, perfluoroalkanes such as perfluoropentane, perfluorohexane, perfluorononane, perfluorohexyl bromide, perfluorooctyl bromide, and perfluorodecyl bromide, perfluoroalkenes such as bisperfluorobutylethylene, perfluorocycloalkanes such as perfluorodecalin, perfluorocyclohexanes, perfluoroadamantane, perfluorobicyclodecane, and perfluoromethyl decahydroquinoline, perfluoro amines such as perfluoroalkyl amines, and C1-C8 substituted compounds thereof, isomers thereof, and combinations thereof. In one embodiment, the fluid may also be combined with a drug.

Next, the fluid is delivered to first tissue chamber 44 through first fluid circuit 48 by alternately tilting microfluidic device 10 between the forward tilted position (FIG. 2A) and to the reverse tilted position (FIG. 2B), with respect to horizontal axis A of microfluidic device 10, respectively. Alternately tilting microfluidic device 10 allows for the fluid to be delivered by gravity, although in other embodiments a pump may be utilized to deliver the fluid. Microfluidic device 10 may be tilted between about 5 and about 90 degrees about horizontal axis A. In one embodiment, microfluidic device 10 is tilted about 18 degrees about horizontal axis. The tilting may be performed by placing microfluidic device 10 on a rocker platform device, by way of example.

First fluid circuit 48 directs a flow of fluid from first inlet reservoir 32(1), through fluid passage 38(1) into microfluidic channel 42(1), through first tissue culture chamber 44 into microfluidic channel 42(2), and through fluid passage 38(2) (via capillary action forces), to first outlet reservoir 34(1) when microfluidic device 10 is in a forward tilted position with respect to horizontal axis A, as shown in FIG. 2A. The fluid flow is the result of the change in height of the fluid within first inlet reservoir 32(1) and first outlet reservoir 34(1) as a result of the change in angle.

First fluid circuit 48 directs the flow of fluid from first outlet reservoir 34(1), through fluid passage 38(3) into microfluidic channel 42(3), into fluid passage 38(4) (via capillary action forces), and back to first inlet reservoir 32(1) when microfluidic device 10 is tilted in a reverse tilted position with respect to horizontal axis A, as shown in FIG. 2B. The fluid flow is the result of the change in height of the fluid within first inlet reservoir 32(1) and first outlet reservoir 34(1) as a result of the change in angle. The flow through microfluidic channel 42(3), which is not in fluid communication with first tissue culture chamber 44, provides a backflow circuit to provide unidirectional flow through the first tissue culture chamber 44 using gravity to drive the flow. Since liquid levels in each of first inlet reservoir 32(1) and first outlet reservoir 34(1) change over time, microfluidic device is tilted back and forth at regular time intervals, such as every 60 seconds.

In the embodiment with first microfluidic component 16 and second microfluidic component provided in a stacked arrangement, the fluid is delivered to second tissue chamber 54 through second fluid circuit 58 as a result of the alternate tilting of microfluidic device 10 between the forward tilted position (FIG. 3A) and to the reverse tilted position (FIG. 3B), with respect to horizontal axis A of microfluidic device 10, respectively. Alternately tilting microfluidic device 10 allows for the fluid to be delivered to second tissue chamber 54 by gravity, although in other embodiments a pump may be utilized to deliver the fluid.

Second fluid circuit 58 directs a flow of the fluid from second inlet reservoir 32(2), through fluid passage 39(1) into microfluidic channel 42(4), through hole 47(1) to microfluidic channel 52(1), through second tissue culture chamber 54 into microfluidic channel 52(2), through hole 47(2) into microfluidic channel 42(5), through fluid passage 39(2) (via capillary action forces) to second outlet reservoir 34(2), when microfluidic device 10 is in a forward tilted position with respect to horizontal axis A, as shown in FIG. 2A. The fluid flow is the result of the change in height of the fluid within second inlet reservoir 32(2) and second outlet reservoir 34(1) as a result of the change in angle.

Second fluid circuit directs the flow of fluid from second outlet reservoir 34(2), through fluid passage 39(3) to microfluidic channel 42(6), and through fluid passage 39(4) (via capillary action forces) back to second inlet reservoir 32(2) when microfluidic device 10 is tilted in a reverse tilted position with respect to horizontal axis A, as shown in FIG. 3B. The fluid flow is the result of the change in height of the fluid within second inlet reservoir 32(2) and second outlet reservoir 34(2) as a result of the change in angle. The flow through microfluidic channel 42(6), which is not in fluid communication with second tissue culture chamber 54, provides a backflow circuit to provide unidirectional flow through the second tissue culture chamber 54 using gravity to drive the flow. Since liquid levels in each of second inlet reservoir 32(2) and second outlet reservoir 34(2) change over time, microfluidic device is tilted back and forth at regular time intervals, such as every 60 seconds.

A further aspect of the invention relates to a method of delivering a fluid to a tissue culture. This method involves seeding a first cellular tissue in a first tissue culture chamber of a first microfluidic component comprising one or more microfluidic channels on a surface thereof and a first tissue culture chamber configured to house the first cellular tissue coupled to at least one of the one or more microfluidic channels. The first microfluidic component with the seeded first tissue culture is inserted into a microfluidic device and the microfluidic device is sealed. A fluid is provided in a first inlet reservoir and a first outlet reservoir of the microfluidic device. The one or more microfluidic channels and the first tissue culture chamber are positioned in fluid communication with the first inlet reservoir and the first outlet reservoir through a first set of fluid passages to form a first fluid circuit. The fluid is delivered to the first tissue chamber through the first fluid circuit of the microfluidic device by alternately tilting the microfluidic device between a forward tilted position and a reverse tilted position, with respect to a horizontal axis of the microfluidic device, respectively.

Yet another aspect of the present invention relates a method of simulating human metabolism in a microfluidic device. This method involves seeding a GI tract tissue in a first tissue culture chamber of a first microfluidic component comprising one or more microfluidic channels on a surface thereof and a first tissue culture chamber configured to house the first cellular tissue coupled to at least one of the one or more microfluidic channels. A liver tissue is seeded in the second tissue culture chamber of a second microfluidic component comprising another one or more microfluidic channels on a surface thereof and a second tissue culture chamber configured to house a second tissue culture coupled to at least one of the another one or more microfluidic channels. The first microfluidic component with the seeded GI tract tissue and the second microfluidic component with the seeded liver tissue are inserted into the microfluidic device in a stacked arrangement and the microfluidic device is sealed. A fluid is provided in a first inlet reservoir and a first outlet reservoir of the microfluidic device. The one or more microfluidic channels and the first tissue culture chamber are positioned in fluid communication with the first inlet reservoir and the first outlet reservoir through a first set of fluid passages to form a first fluid circuit. The fluid is provided in a second inlet reservoir and a second outlet reservoir of the microfluidic device. The another one or more microfluidic channels and the second tissue culture chamber are positioned in fluid communication with the second inlet reservoir and the second outlet reservoir through a second set of fluid passages to form a second fluid circuit. The fluid is delivered to the first tissue chamber through the first fluid circuit of the microfluidic device and to the second tissue chamber through the second fluid circuit by alternately tilting the microfluidic device between a forward tilted position and a reverse tilted position, with respect to a horizontal axis of the microfluidic device, respectively. Additional microfluidic components may be added representing additional organs with other seeded tissue cultures as required.

A low-cost microfluidic body-on-a-chip platform that replicates the relationship between the GI tract epithelium, liver tissue, and blood volume of the human body in a scaled down, near-physiologic way was developed. In the human body, the GI tract epithelium and the liver are responsible for the first pass metabolism of nutrients and drugs, sometimes diminishing the bioavailability of orally administered drugs significantly. Using the developed system, a coculture of the GI tract epithelial cell line Caco-2 with liver tissue that was constructed from human primary liver cells was established. Liver tissue was constructed as 3D tissue from a mixture of human primary nonparenchymal cells (fibroblasts, stellate and Kupffer cells) and human primary hepatocytes. The blood volume of the human body was represented by cell culture medium.

Another aspect of the present invention relates to a method for determining a pharmacokinetic, a pharmacodynamic, or a pharmacokinetic-pharmacodynamic (PKPD) effect of an agent on a cellular tissue. This method involves providing the microfluidic device according to the present invention and seeding the cellular tissue in the first tissue culture chamber of the first microfluidic component. The first microfluidic component with the seeded first tissue culture is inserted into the chamber of the base. The chamber is sealed by reversibly coupling the sealing member to the base. A fluid comprising the agent is provided in the first inlet reservoir and the first outlet reservoir of the sealing member. The fluid comprising the agent is delivered to the first tissue chamber through the first fluid circuit by alternately tilting the microfluidic device between the forward tilted position and to the reverse tilted position, with respect to the horizontal axis, respectively. A pharmacokinetic, a pharmacodynamic, or a pharmacokinetic-pharmacodynamic assay is performed on the cellular tissue after the delivering. One or more in vitro pharmacokinetic or pharmacodynamic effects of the agent on the cellular tissue are determined based on the assay. In one example, the first microfluidic component can represent the liver while the second microfluidic component represent another organ system, such as the GI tract, by way of example only. Additional microfluidic components representing other organs with other seeded tissues can also be added.

EXAMPLES

Example 1

Materials and Methods

1) Organ Chamber Dimensions

Data for the sizes of human organs, blood flow through each organ, and blood distribution in the body were obtained from a collection of human data by Davies et al., "Physiological Parameters in Laboratory Animals and Humans," *Pharm. Res.*, 10:1093-1095 (1993) and Price et al., "Modeling Interindividual Variation in Physiological Factors Used in PBPK Models of Humans," *Crit. Rev. Toxicol.*, 33:469-503 (2003). the disclosures of which are incorporated by reference herein in their entirety. Organ chamber volumes for the device were calculated to be 1/95 000th of those in vivo organ volumes. Final organ chamber volumes on each organ chip are 12.9 mm$^3$ for the GI tract chamber and 16.5 mm$^3$ for the liver chamber.

2) Microfluidic Channel Dimensions

The two organ chips were constructed with each containing a fluidic circuit. The GI tract chip contained a fluidic channel that perfused the apical side of the GI tract epithelium, and the liver chip contained a fluidic channel that perfused the liver chamber as well as the basolateral side of the GI tract epithelium. When assembled into a multi-organ system the GI tract epithelium and liver were connected with each other through a porous membrane that allowed soluble metabolite exchange between the two tissues. The fluidic channel that supplied the liver chamber plus the basolateral side of the GI tract epithelium represents part of the body's systemic circulation, i.e. the medium in it is the blood surrogate. The medium in the apical chamber of the GI tract epithelium represents the liquid present in the GI tract lumen. Medium flow within both organ chips of the device was driven via gravity. Height differences between inlets and outlets were created by placing the device on a rocker platform. Flow rates were controlled passively via the hydraulic resistances of the microfluidic channels on each organ chip. The dimensions of each fluidic circuit were designed so that the hydraulic resistances of all elements in it result in a flow rate that is close to the physiologic value, i.e. close to the flow rate of blood within a tissue section of the size of the organ chamber. In the human body, 14 µL of blood perfuse a liver volume of the size of 16.5 mm$^3$ per minute, and 10 µL of blood perfuse a GI tract volume of the size of 12.9 mm$^3$.

Gravity was utilized to drive fluidic flow and control the rate of flow passively via hydraulic resistances of microfluidic channels. To control the fluid flow, the dimensions of each fluidic circuit were designed so that the hydraulic resistance of all elements in the fluidic circuit limit the flow rate to the physiologic values. Hence, channel dimensions are different for each organ chamber in the system. Since liquid levels in each of the reservoirs change over time and the platform is tilted back and forth at a time interval of 60 seconds, the flow rate does not reach steady state. The device was designed so that the flow rate averaged over 60 seconds is the scaled flow rate needed.

3) Microfabrication

The platform and two organ chips were designed with Solidworks (SolidWorks Corp., Waltham, Mass., USA) and printed with a 3D object printer (ObJet 30Pro, Stratasys Ltd., Rehovot, Israel) using the provided Veroclear polymer. The printed devices were cured for 48 hours at 40° C. under vacuum and then coated with 5 g of parylene C using a coater from SCS Equipment (Dallas, Tex., USA, Model PDS 2010 Labcoater). The platform consisted of two housing pieces (top and bottom) into which the two organ chips fit. Once assembled, the two organ chips are connected with the reservoirs and valve mechanism that supply medium at near physiologic flow rates. Each of the two organ chips was assembled from two 3D printed polymer pieces. Porous polycarbonate membranes (Sterlitech Corp., catalog #P/N PCT45025100) were sandwiched between these two pieces. The GI tract tissue was cultured directly on that porous membrane. On the liver chip, a woven nylon scaffold (RegeneMed, Inc.) was inserted above the porous polycarbonate membrane, providing the 3D culture environment for the liver tissue as previously described. When the organ chips were stacked on top of each other in the platform, the porous membranes enabled communication between the basolateral side of the GI tract tissue and the liver tissue, mimicking the close connection these two tissues experience in vivo.

4) GI Tract Tissue Construction

Caco-2 cells were maintained in cell culture flasks using DMEM with 20% FBS at 37° C. and 5% $CO_2$. 16 days prior to the assembly of the devices, the cells were lifted using trypsin and seeded onto the porous membrane of the GI tract chip at a concentration of 100,000 cells per cm$^2$. The cell-loaded chips were placed into petri dishes and maintained for 16 days using DMEM with 20% FBS at 37° C. and 5% $CO_2$.

5) Liver Tissue Construction 3D liver tissues were constructed on liver chips using 3D scaffolds that were placed into the liver tissue culture chambers. The scaffolds were obtained from RegeneMed Inc. (San Diego, Calif.). They consist of two layers of interwoven polymer fibers that together create a 3D mesh structure. Primary human hepatocytes and non-parenchymal cells (a mixture of primary human fibroblasts, stellate cells, Kupffer cells, sinusoidal endothelial cells, and vascular and biliary epithelial cells) were obtained from Regenemed Inc. (San Diego, Calif.). Nine days prior to device assembly, non-parenchymal cells (NPC) were thawed and seeded onto 3D scaffolds that were placed in the organ chamber of the liver chips. The seeding concentration of NPC was 150 000 cells per liver chip. The chips with NPC cell cultures were placed in Petri dishes and maintained for 7 days in a humidified 5% $CO_2$ incubator at 37° C. to allow the NPC to express extracellular matrix proteins and growth factors necessary to support hepatocyte function. The cultures were sustained with medium obtained from RegeneMed Inc. (#L3 SNB-500, RegenMed, San Diego, Calif.). On day 7 after NPC seeding, cryopreserved primary human hepatocytes were thawed and seeded onto the liver chip at a concentration of 250 000 cells per scaffold. After 48 hours of maintaining these mixed cell cultures in Petri dishes, the cell-loaded chips were ready for use.

6) Device Assembly and Operation

When both GI tract and liver tissues were mature (Caco-2 cells after 16 days and 3D liver tissues after 9 days of on-chip culture in Petri dishes) one of each of the GI tract and liver chips was aseptically transferred into the cavity of the bottom platform piece. The devices were closed, covered with sterilized lids, and transferred onto a rocking platform that was placed into an incubator. The device was rocked back and forth every 60 seconds, facilitating perfusion by creating a height difference in liquid levels in each of the two reservoir sets. The rocking platform tilted between angles of ±18°, resulting in periodic, unidirectional, gravity-induced medium flow through the organ chambers for 60 seconds in intervals of 120 seconds. Prior to transfer, the two platform pieces were sterilized with 70% ethanol for 24 hours and washed with PBS. The device was filled with cell culture medium and closed without encapsulating air bubbles using the top piece. The two wells that supplied the apical side of the GI tract tissue were filled with 150 µL of Caco-2 medium (DMEM with 10% FBS), and the two wells that supplied the systemic circulation circuit were filled with 150 µL of liver cell medium (#L3SNB-500, RegenMed, San Diego, Calif.). The medium was renewed in all four reservoirs (150 µL) every day for 14 days and the medium was recovered from the systemic circulation circuit and analyzed for metabolites produced in the liver (urea and albumin) and for liver viability markers (AST).

7) Liver Cell Viability

To determine the viability of liver cells throughout the 14 day co-culture period the amounts of aspartate aminotransferase, (AST, a cytosolic enzyme) in the medium taken from the systemic circulation loop of the device were measured. Testing was performed at the clinical pathology laboratory in the Animal Health Diagnostic Center at Cornell University, using an automated chemistry analyzer (Hitachi Modular P, Roche Diagnostics) with manufacturer's reagents. Measuring AST levels allowed quantification of the amount of liver cell death, and albumin and urea production per number of live liver cells to be expressed.

8) (Transepithelial Cell Layer Resistance Measurements)

GI tract tissue function can be measured via the transepithelial cell layer resistance (TEER). For the purpose of conducting these measurements on-chip and throughout the 14 day co-culture period, custom-made Ag/AgCl electrodes were integrated into the cell culture platform. The electrodes were constructed from 3 mm thick, hollow silver tubes and silver chloride electrodes purchased from A-M Systems (Sequim, Wash. catalog #550008). A World Precision Instrument (Millicell ERS-2) was used to measure the TEER daily. It should be noted that the electric field produced in custom-made systems can differ from that produced in commercially available measuring cups. TEER values measured with custom-build systems cannot be directly compared to those measured with commercial cups. Since the second TEER electrode is located beneath the liver tissue control measurements were conducted resulting in the finding that the liver scaffold and tissue do not contribute to the TEER value, i.e. the reading without GI tract tissue is zero.

9) Rates of Urea and Albumin Synthesis

200 µL of cell culture medium (100 µL from each well) were collected from the systemic circulation circuit of the devices on day 3, 7, 10, and 14 of the co-culture with day 1 corresponding to the first day of co-culture in the device. Urea concentrations in the medium were measured using a DIUR assay kit, which was used as suggested by the manufacturer (BioAssay Systems, Hayward, Calif., USA, QuantiChrom catalog #DIUR-500). 50 µL of medium was transferred into the wells of a 96 well plate, chromogenic reagent was added that forms a stable colored complex specifically with urea, and the optical density of the solution was measured within 5 minutes of adding the chromogenic reagent at 520 nm using a spectrophotometer. The results were compared to a standard curve and are expressed as µg per day per million cells.

Albumin synthesis was evaluated by enzyme-linked immunosorbent assay (ELISA), using a kit and following the manufacturer's directions (Bethyl Laboratories, Inc., Montgomery, Tex., USA, catalog #E80-129). The wells of a 96-well plate were coated with goat anti-human albumin antibody and washed with buffer. 100 µL medium taken from the cell culture devices was transferred into the wells. After incubation, HRP-conjugated goat anti-human antibody was added to the wells and incubated for 1 hour. Following a washing step with buffer, 100 µL of enzyme substrate (tetramethylbenzidine) was added and incubated for 15 minutes. After adding stopping solution, the absorbance of the solution was measured using a plate reader at 450 nm.

10) P450 Enzyme Activity

CYP450 enzyme activity in the liver chip was monitored throughout the 14 day co-culture period using Promega Glo assays (Promega Corp., Madison, Wis., USA, catalog #V9002 for CYP3A4 and catalog #V8752 for CYP1A1). These nondestructive assays allow repeat CYP450 induction measurements on the same cultures. Briefly the induction reagent (10 µM of rifampicin for CYP3A4 and 1 µM of 3-methylcholanthrene for CYP1A1 induction) was diluted in medium and added to the two reservoirs that served the systemic circulation circuit for 72 hours. The reservoirs were then washed with buffer three times for 5 minutes and subsequently the buffer was replaced with IPA-luciferin. Separate devices were used for measuring the induction of each enzyme. At the end of the incubation period, medium was collected and transferred into the wells of a 96 well-plate. Detection reagent was added and luminescence was read with a Veritas luminometer using the settings provided by the manufacturer. Results were expressed as multiples of the level of induction observed in vehicle controls without induction reagents.

11) Statistical Analysis

Each data point plotted in graphs represents the mean of three separate experiments±standard deviation. Multiple means were compared with a one-way ANOVA, followed by a Bonferroni correction for the number of pair-wise comparisons (JMP software). Comparison of two values with each other was performed using Student's t-tests. A p value of <0.05 was considered significant.

Example 1

Results

Low amounts of aspartate aminotransferase (AST, ~10-17.5 U/L) in the cell culture medium and transepithelial resistances (TEER) across the GI tract epithelial layer of 250 to 650 $\Omega cm^2$ indicate that the cells retained high viability and functionality throughout the 14-day period of co-culture in the device. Metabolic rates of hepatocytes were comparable to those of hepatocytes in other fluidic cell culture systems (albumin production ranged between 3-6 µg/day per million hepatocytes and urea production ranged between 150-200 µg/day per million hepatocytes).

1) Passive Device Operation

The device was designed so that the fluidic flow through each of the two organ chambers was controlled via the hydraulic resistances of the microfluidic circuits. At a constant tilting angle at +18° flow rates change over the course of 60 seconds for which the angle is held. The device is then tilted on a rocker platform in the other direction for 60 seconds to refill the inlet reservoir with medium. The liquid levels in each of the reservoirs change over the course of the 60 second hold time, meaning that Δh between the liquid levels in the two reservoirs changes over time. The flow rate does not reach steady state and the average flow rate was measured over 60 seconds. The average flow rate was 20.5±0.7 µL min−1 for the blood surrogate (i.e. cell culture medium) in the systemic circulation circuit, supplying the basolateral GI tract chamber and liver chamber, and 24.5±0.9 µL min−1 in the apical GI tract chamber. The total medium volume in the systemic circulation circuit represents the blood volume of the human body, scaled by a factor of 95,000 (this volume is 61.3 µL), plus additional liquid that is required to operate the device (this additional volume is 260 µL).

2) Liver Cell Viability

Medium was recovered from the systemic fluidic circuit and analyzed for the cytosolic enzyme aspartate aminotransferase (AST). Throughout the 14 day co-culture period low amounts of AST (~10-17.5 U L−1) were measured as shown in FIG. 6A, indicating high cellular viability in the liver tissue as discussed in Esch et al., "Body-on-a-Chip Simulation With Gastrointestinal Tract and Liver Tissues Suggests that Ingested Nanoparticles Have the Potential to Cause Liver Injury," *Lab Chip*, 14:3081-3092 (2014), the disclosure of which is incorporated herein by reference in its entirety. This high level of liver cell viability was maintained for the 14 day duration of the co-culture within the platform (FIG. 6A).

3) GI Tract Epithelium Integrity: TEER Measurements

Figure 6B:
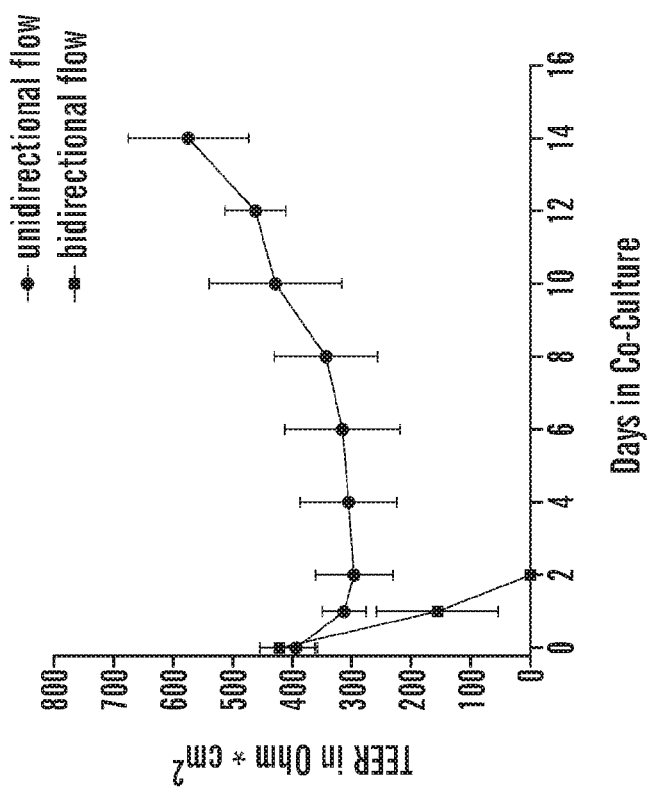
FIGS. 6A and 6B illustrate experimental results for amounts of aspartate aminotransferase (AST) released into the cell culture medium, measured throughout a 14 day co-culture period (FIG. 6A) and TEER across the Caco-2 cell layer measured under unidirectional and bidirectional medium flow throughout the 14 day co-culture period (FIG. 6B). Values are means±standard deviations, with n=3 and each separate experiment consisting of two to three technical replicates.
Figure 6A:
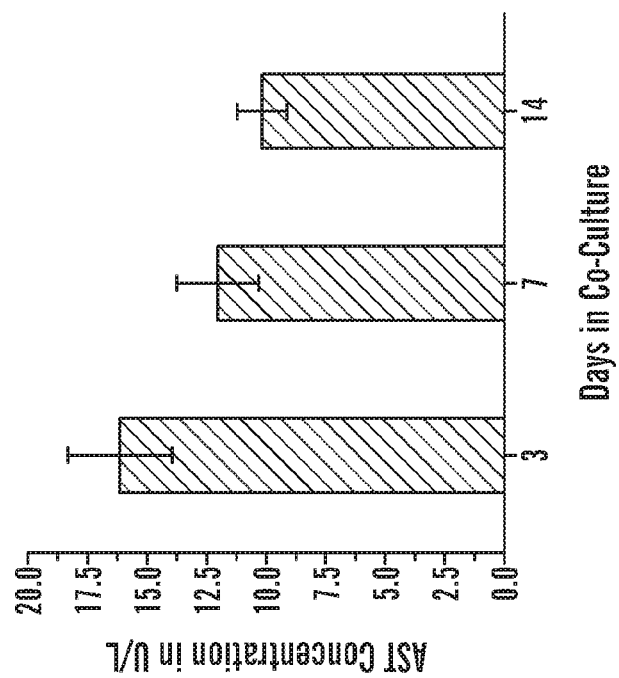

The measured TEER under unidirectional medium flow was lowest right after device assembly and then rose over time from about 250 ohms×cm$^2$ to about 650 ohms×cm$^2$ as shown in FIG. 6B. Under bidirectional medium flow, TEER values dropped to zero after 48 hours of device operation (FIG. 6B). Since Caco-2 cells are sensitive to the direction of flow, the performance of the integrated valves can be judged by the TEER. The observed results provide evidence for the assumption that under unidirectional flow the cells maintained their barrier function throughout the 14 day co-culture period. A relatively high variability was observed when measuring TEER, perhaps reflecting slightly different degrees of cell layer maturity at the point of device assembly.

4) Albumin and Urea Production

Figure 7A:
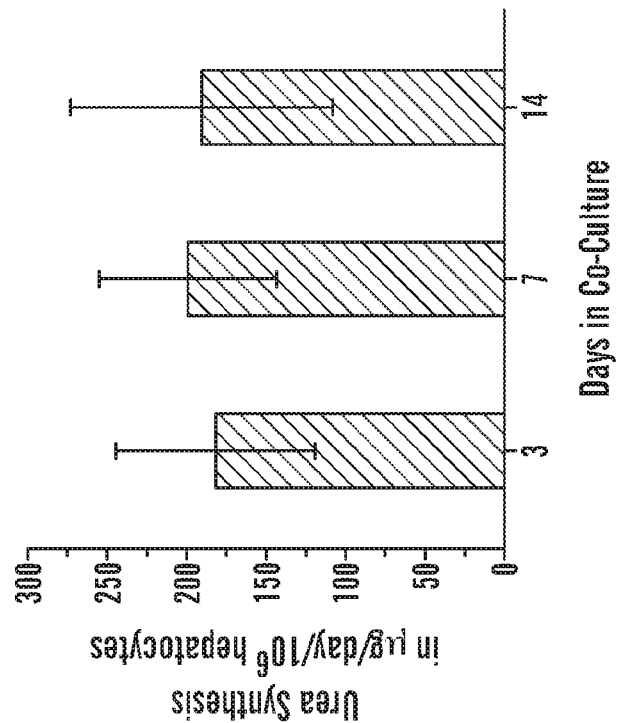
FIGS. 7A and 7B illustrate experimental results for rates of albumin (FIG. 7A) and urea (FIG. 7B) production throughout the 14 day co-culture period. Values are represented as means±standard deviations, with n=3 and each experiment consisting of two to three technical replicates. Significant differences (p>0.05) were not detected between the days on which albumin and urea production were measured.
Figure 7B:
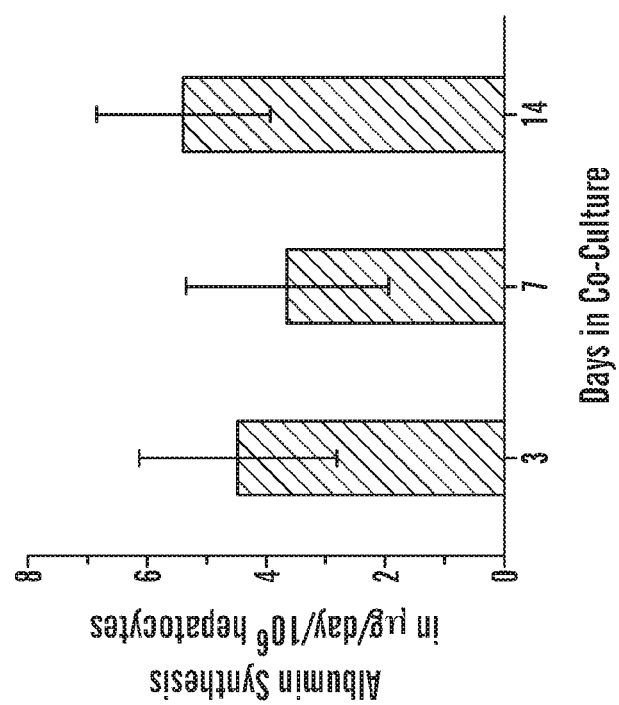

To assess the metabolic activity of the cells when maintained within the body-on-a-chip device, the hepatocytes' average production of albumin and urea per million cells per day was measured. The cells produced albumin at an average rate of 3-6 µg/million cells per day, and urea at an average rate of 150-200 µg/million cells per day as illustrated in FIGS. 7A and 7B. Rates of this magnitude were previously observed with microfluidic liver cultures as described in Esch et al., "Multi-Cellular 3D Human Primary Liver Cell Culture Elevates Metabolic Activity Under Fluidic Flow," *Lab Chip*, 15:2269-2277 (2015), the disclosure of which is hereby incorporated herein by reference in its entirety. The measured metabolic activity remained at constant levels over the period of 14 days, indicating that sufficient nutrient and gas exchange took place over the cell culture period.

5) CYP Enzyme Activity

Figure 8:
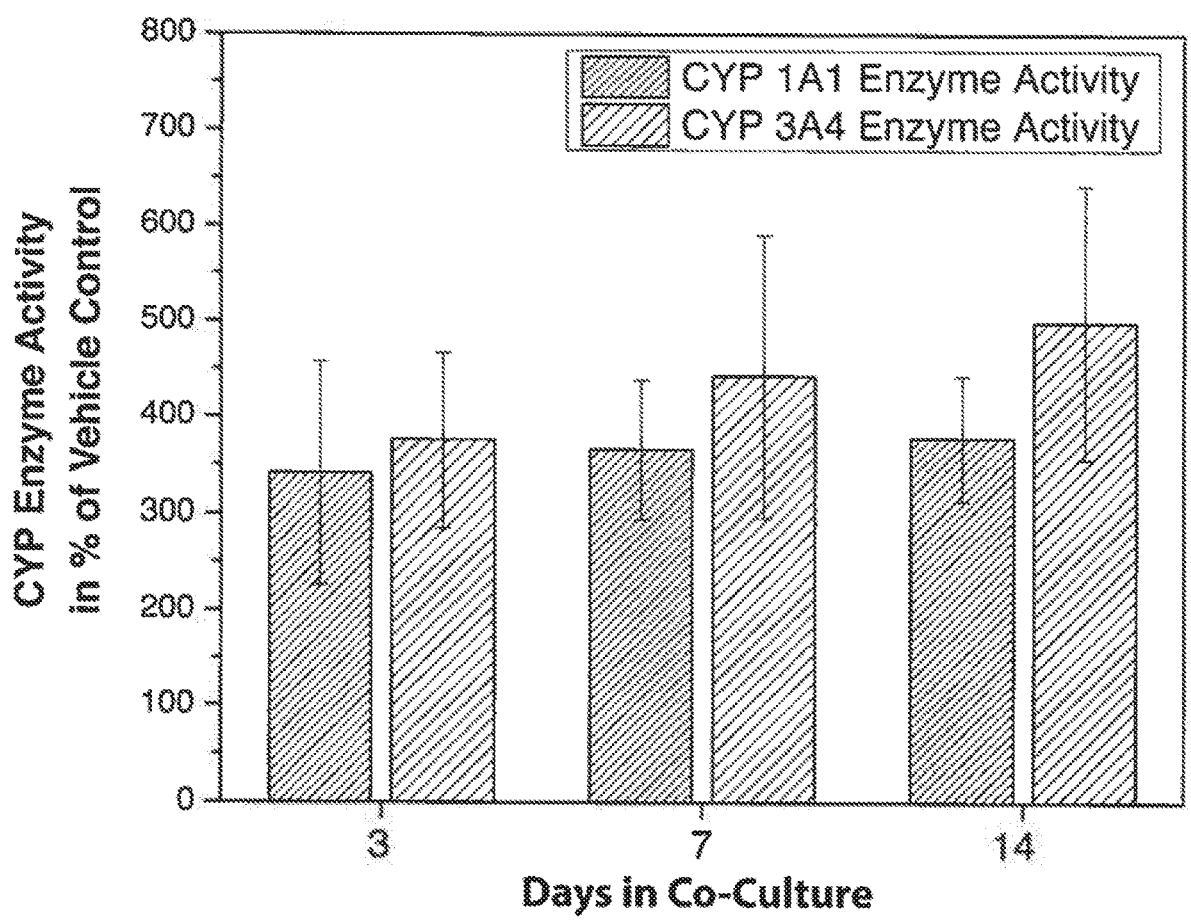
FIG. 8 illustrate experimental results for activity of CYP 1A1 and CYP 3A4 enzymes throughout the 14 day co-culture period. Values are shown as percent increase compared to cultures treated with vehicle controls. Values are means±standard deviations, with n=3. Significant differences (p>0.05) between days on which CYP enzyme activity was measured were not detected.

To test the ability of the liver tissue to respond to toxic substances, the activity of CYP enzymes (CYP 1A1, and CYP 3A4) was induced. Both enzymes were active at levels between 350-500% of that of cells that were treated with vehicle controls as illustrated in FIG. 8.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A microfluidic device comprising:
a base comprising a base chamber;
a sealing member removably coupled to the base to provide a seal for the chamber, the sealing member comprising a body and a first inlet reservoir and a first outlet reservoir, wherein the first inlet reservoir and the first outlet reservoir are positioned within the body and communicating with the base chamber through a first set of fluid passages in the sealing member when the sealing member is coupled to the base; and
a first microfluidic component removably within the base chamber, the first microfluidic component comprising one or more microfluidic channels on a surface thereof and a first tissue culture chamber configured to house a first tissue culture coupled to at least one of the one or more microfluidic channels, wherein the one or more microfluidic channels comprise a first microfluidic channel in fluid communication with the first tissue culture chamber at a first end of the first tissue chamber, a second microfluidic channel in fluid communication with the first tissue culture chamber at a second end of the first tissue culture chamber opposite the first end, and a third microfluidic channel located separately on the first microfluidic component from the first microfluidic channel and the second microfluidic channel and not in fluid communication with the first tissue culture chamber, the first microfluidic channel, or the second microfluidic channel, wherein, when the first microfluidic component is within the base chamber, the one or more microfluidic channels and the first tissue culture chamber are positioned in fluid communication with the first inlet reservoir and the first outlet reservoir through the first set of fluid passages in the sealing member to form a first fluid circuit for directing a first flow of fluid from the first inlet reservoir, through the first tissue culture chamber, to the first outlet reservoir, and from the first outlet reservoir back to the first inlet reservoir upon tilting the microfluidic device to a forward tilted position and to a reverse tilted position, with respect to a horizontal axis, respectively, wherein the first flow of fluid to the first tissue chamber from the first fluid circuit is unidirectional when the microfluidic device is moving between the forward tilted and reverse tilted positions.

2. The microfluidic device as set forth in claim 1, wherein the first fluid circuit is configured to provide a first flow rate of the first flow of fluid to the first tissue culture chamber substantially similar to a first physiological flow rate in a first organ.

3. The microfluidic device as set forth in claim 1, wherein the one or more microfluidic channels have a width of about 5 µm to about 5 mm.

4. The microfluidic device as set forth in claim 1, wherein the first set of fluid passages comprise:
a first capillary channel extending from the first inlet reservoir to the first microfluidic channel;
a second capillary channel extending from the second microfluidic channel to the first outlet reservoir to form the first fluid circuit from the first inlet reservoir, through the first tissue culture chamber, to the first outlet reservoir;
a third capillary channel extending from the first outlet reservoir to the third microfluidic channel; and a fourth capillary channel extending from the third microfluidic channel to the first inlet reservoir to form a first backflow circuit between the first outlet reservoir and the first inlet reservoir.

5. The microfluidic device as set forth in claim 1, wherein the sealing member further comprises a threaded stem configured to mate with a corresponding threaded portion in the base to reversibly couple the sealing member to the base.

6. The microfluidic device as set forth in claim 1, wherein the sealing member further comprises a first alignment mechanism configured to align the one or more channels of the first microfluidic component with the first inlet reservoir and the first outlet reservoir.

7. The microfluidic device as set forth in claim 1, wherein the first microfluidic component further comprises a first porous membrane in the first tissue culture chamber to support tissue growth.

8. The microfluidic device as set forth in claim 1 further comprising:
a second microfluidic component removably within the base chamber in a stacked arrangement with the first microfluidic component, the second microfluidic component comprising another one or more microfluidic channels on a surface thereof and a second tissue culture chamber configured to house a second tissue culture coupled to at least one of the another one or more microfluidic channels.

9. The microfluidic device as set forth in claim 8, wherein the base chamber further comprises:
a second inlet reservoir and a second outlet reservoir positioned within the body and communicating with the base chamber through a second set of fluid passages in the sealing member when the sealing member is coupled to the base, wherein, when the second microfluidic component is within the base chamber, the another one or more microfluidic channels and the second tissue culture chamber are positioned in fluid communication with the second inlet reservoir and the second outlet reservoir through the second set of fluid passages in the sealing member to form a second fluid circuit for directing a second flow of fluid from the second inlet reservoir, through the second tissue culture chamber, to the second outlet reservoir, and from the second outlet reservoir back to the second inlet reservoir upon tilting the microfluidic device to the forward tilted and to the reverse tilted position, with respect to the horizontal axis, respectively, wherein the second flow of fluid to the second tissue culture chamber from the second fluid circuit is unidirectional when the microfluidic device is moving between the forward tilted and reverse tilted positions.

10. The microfluidic device as set forth in claim 9, wherein the second fluid circuit is configured to provide a second flow rate of the second flow of fluid to the second tissue culture chamber substantially similar to a second physiological flow rate in a second organ.

11. The microfluidic device as set forth in claim 9, wherein the another one or more microfluidic channels further comprise:
a fourth microfluidic channel in fluid communication with the second tissue culture chamber at a first end of the second tissue culture chamber;
a fifth microfluidic channel in fluid communication with the second tissue culture chamber at a second end of the second tissue culture chamber opposite the first end;
a sixth microfluidic channel positioned to receive the second flow of fluid from the second inlet reservoir and having a first hole in fluid communication with the fourth microfluidic channel of the second microfluidic component;
a seventh microfluidic channel having a second hole in fluid communication with the fifth microfluidic channel of the second microfluidic component; and
an eighth microfluidic channel positioned separately from sixth and seventh microfluidic channels and not in fluid communication with either the sixth or seventh microfluidic channels.

12. The microfluidic device as set forth in claim 11, wherein the second microfluidic component comprises a second alignment mechanism to align the first hole in the sixth microfluidic channel with sixth microfluidic channel and the second hole of the seventh microfluidic channel with the fifth microfluidic channel.

13. The microfluidic device as set forth in claim 11, wherein the second set of fluid passages comprise:
a fifth capillary channel extending from the second inlet reservoir to the sixth microfluidic channel;
a sixth capillary channel extending from the seventh microfluidic channel to the second outlet reservoir to form the second fluid circuit from the second inlet reservoir, through the sixth microfluidic channel, through the first hole, through the fourth microfluidic channel, through the second tissue culture chamber, through the fifth microfluidic channel, through the second hole, through the seventh microfluidic channel, to the second outlet reservoir;
a seventh capillary channel extending from the second outlet reservoir to the eighth microfluidic channel; and
an eighth capillary channel extending from the eighth microfluidic channel to the second inlet reservoir to form a second backflow circuit between the second outlet reservoir and the second inlet reservoir.

14. The microfluidic device as set forth in claim 1 further comprising:
a first electrode located in the base and a second electrode located in the sealing member, wherein the first electrode and the second electrode are positioned to provide a current across the base chamber.

* * * * *